(12) United States Patent
Caffrey

(10) Patent No.: US 6,284,765 B1
(45) Date of Patent: Sep. 4, 2001

(54) (+) NALOXONE AND EPINEPHRINE COMBINATION THERAPY

(75) Inventor: James L. Caffrey, Burleson, TX (US)

(73) Assignee: The University of North Texas Health Science Center at Fort Worth, Fort Worth, TX (US)

( * ) Notice: Subject to any disclaimer, the term of this patent is extended or adjusted under 35 U.S.C. 154(b) by 0 days.

(21) Appl. No.: 09/561,391

(22) Filed: Apr. 27, 2000

(51) Int. Cl.$^7$ .......................... A61K 31/52; A61K 31/44; A61K 31/135
(52) U.S. Cl. ...................... 514/263; 514/289; 514/653
(58) Field of Search .................. 514/263, 289, 514/653

(56) References Cited

U.S. PATENT DOCUMENTS

| | | | |
|---|---|---|---|
| 4,141,897 | 2/1979 | Olofson et al. | 546/45 |
| 4,434,168 | 2/1984 | Holaday et al. | 424/260 |
| 4,464,378 | 8/1984 | Hussain | 424/260 |
| 4,521,601 | 6/1985 | Rice | 546/45 |
| 5,668,265 | 9/1997 | Nadeau et al. | 536/23.1 |
| 5,817,679 | 10/1998 | Shen et al. | 514/339 |
| 5,854,269 | 12/1998 | Haslwanter et al. | 514/385 |
| 5,866,154 | 2/1999 | Bahal et al. | 424/423 |
| 5,958,379 | 9/1999 | Regenold et al. | 424/47 |
| 6,026,817 | 2/2000 | Clemens | 128/898 |

OTHER PUBLICATIONS

Circulatory Shock 31:317–322 (1990) Naloxone Potenetiates Contractile Responses to Epinephrine in Isolated Canine Arteries.
Circulatory Shock 40:206–211 (1993) (+) Naloxone Potentiates the Inotropic Effect of Epinephrine in the Isolated Dog Heart.

*Primary Examiner*—Raymond Henley, Jr.
(74) *Attorney, Agent, or Firm*—Bracewell & Patterson, LLP

(57) ABSTRACT

A composition formulated for dose-wise delivery to a breathing passageway of a human, the composition comprising a carrier solution containing (+)naloxone and a pharmacologically effective amount of at least one adrenergic agonist, the (+)naloxone and agonist forming a mixture in the carrier. The at least one adrenergic agonist is selected from the group consisting of epinephrine, isoproterenol, albuterol, aminophylline, beclomethasone, dyphylline, flunisolide, isoetharine, metaproterenol, oxtriphylline, terbutaline, theophylline, pseudoephedrine, phenylephrine, ephedrine and norepinephrine. That composition is delivered by an atomizer means such as a liquid sprayer or inhaler to treat nasal congestion and asthmatic attacks. Further provided by the invention is a cardiovascular and respiratory stimulating composition for administration to a patient in doses, the composition comprising a pharmacologically effective concentration of (+)naloxone in a carrier solution. If necessary, the composition may also contain a pharmacologically effective amount of at least one adrenergic agonist.

32 Claims, 3 Drawing Sheets

(+) NALOXONE AND EPINEPHRINE COMBINATION THERAPY

BACKGROUND OF THE INVENTION

1. Field of the Invention

The present invention is a composition for and method of alleviating nasal congestion or lung ailments, and for providing energy to persons in emergency situations. More specifically, the present invention is a therapy comprising the opiate antagonist (+)naloxone in combination with an adrenergic agonist/bronchodilator.

2. Description of the Prior Art

Naloxone is a narcotic antagonist that prevents or reverses the effects of opiates. The compound and methods for its synthesis are described in U.S. Pat. No. 3,254,088 and its use as a narcotic antagonist is described in U.S. Pat. No. 4,267,182. Like many compounds, naloxone is a racemic mixture of stereoisomers, termed (+)naloxone and (−)naloxone. The racemic mixture (+/−), and in particular the (+)enantiomer, have been shown to potentiate inotropic responses to catecholamines such as epinephrine. Caffrey et al., 31 Circulatory Shock 317–332 (1990).

Catecholamines, including epinephrine (adrenaline), norepinephrine (noradrenaline), dobutamine, and isoproterenol, act as adrenergic agonists in exerting inotropic influences on cardiac muscle and on the constriction or relaxation of blood vessels and the relaxation of bronchial muscle in mammals. The major inotropic influences of these agonists is to increase the contractility of cardiac muscle, and stimulate heart rate. Adrenergic agonists also increase the level of blood glucose and improve air flow in the lungs and nasal passageway. These adrenergic agonists are powerful inotropic agents and are potentially useful interventions for treatment of asthmatic attacks, nasal congestion, or to improve energy in persons who are facing emergency situations such as in combat or emergency rescue personnel.

Adrenergic agents are also widely employed locally in the nasal passages to constrict blood vessels and relieve swelling and congestion. Adrenergic agents are also widely used in the lungs and airways to dilate the airways and ease passage of air. There are two major problems in regard to there uses. First, the adrenergic agents can escape from the point of local application in the nose or airways into the general circulation with the potential to contribute to the heart problems cited below. Second, when these agents are used frequently during chronic, reoccurring or protracted episodes of illness, they loose effectiveness. The return or intensification of symptoms often necessitates more frequent application of the medication or an increase in the dose. This leads to a further loss of efficacy and a much greater probability of a significant spread of the agent from the local site into the general circulation. The systemic distribution of the adrenergic agents into the general circulation is associated with a significant cardiovascular risk. This risk significantly limits the use of these agents, especially in patients with any degree of coronary heart disease, cardiac instability, arrhythmia, hypertension, cerebral vascular disease, or any other peripheral vascular disease (e.g. athrosclerosis, Reynauds disease, intermittent claudication, and arterial spasm).

There are important disadvantages to the use of adrenergic agonists to stimulate cardiac, cardiovascular, and cardiopulmonary functions in humans. Potentially lethal cardiac arrhythmias and cardiac necrosis can result due to an imbalance between nutritional supply and energy demand when adrenergic agonists are used in patients. As stated above, this concern is particularly important for those patients with any form of cardiovascular disease. Specifically, adrenergic agonists produce disproportionate increases in cardiac energy requirements relative to increases in function, especially at higher doses, and deplete energy reserves of post-ischemic, failing cardiac muscle. The depletion of the energy reserves is characterized by a decrease in levels of ATP and the free energy of ATP hydrolysis, used to transfer free energy between energy-producing and energy consuming systems within virtually all living organisms.

The harmful effects of using adrenergic agonists may serve to worsen cardiac trauma. In order to avoid the deleterious effects of the agonists, lower concentrations must be used. However, these low dose levels are often ineffective in stimulating the heart or as a bronchodilator. Thus, there is a need for a method of increasing the sensitivity of adrenergic agonists in humans.

When used in conjunction with naloxone, catecholamines can be used in lower doses, thus decreasing the negative effects of adrenergic agonists. This potentiating effect has been shown to occur with the racemic mixture (both the (−)naloxone and (+)naloxone enantiomers). Gu et al., 40 Circulatory Shock, 206–211 (1993). However, another problem arises in using naloxone in that the racemic mixture, and in particular the (−)naloxone enantiomer, acts as an opiate antagonist and thus heightens the pain sensations of the person being treated, and would in fact be contraindicated for those with injuries, those in pain, and/or when opiates such as morphine are being administered simultaneously.

The (+)naloxone enantiomer does not act as an opiate antagonist. Yet, (+)naloxone is an active potentiator of adrenergic agonists. Given this effect, it would be highly desirable to develop a therapy that takes advantage of the benefits of agonists while eliminating the detrimental side effects. In particular, the use of such adrenergic agonists and bronchodilators as epinephrine is highly desirable in treating asthmatic attack, nasal congestion due to cold, allergies, and other diseases involving airway compromise. What is needed is an improved method of treating breathing passageway compromise in humans.

SUMMARY OF THE INVENTION

It is therefore one object of the present invention to provide an improved nasal decongestant.

It is another object of the present invention to provide an improved treatment for asthmatic attacks.

It is yet another object of the present invention to provide a drug therapy wherein the benefits of improved air flow in a human are achieved while avoiding excessive blood vessel constriction.

It is yet another object of the present invention to avoid the use of racemic mixtures of naloxone that may be contraindicated due to pain in the human or where opiates are being concurrently administered.

It is yet another object of the present invention to provide a method of increasing the heart rate, stroke volume, cardiac output blood glucose, blood lipids and blood pressure for a user in an emergency, stressful situation. This would provide strength, endurance, energy, and help prevent fatigue.

It is yet another object of the present invention to support the circulation and improve blood pressure when blood pressure is reduced due to blood loss, trauma, infection, toxins, stress, fear, pain, or allergic reaction.

It is yet another object of the present invention to enhance local vasoconstriction and serve as an adjuvant administered with other pharmaceuticals in order to contain those other pharmaceuticals in a high therapeutically effective concentration at their site of administration. This object of the present invention would also serve to restrict the spread of those other pharmaceuticals to the rest of the body where they might produce undesirable or toxic consequences.

These and other objects are achieved by a composition formulated for dose-wise delivery to a breathing passageway of a human, the composition comprising a carrier solution containing (+)naloxone and a pharmacologically effective amount of at least one adrenergic agonist or bronchodilator (hereinafter "adrenergic agonist" or "agonist"), the (+)naloxone and agonist forming a mixture in the carrier. As an example of an effective amount, the dose of the composition is typically metered to deliver between about 0.01 and 5 µg/mL of the adrenergic agonist and between about 0.1 and 6 µg/mL of (+)naloxone. At least one adrenergic agonist is selected from the group consisting of epinephrine, isoproterenol, albuterol, aminophylline, beclomethasone, dyphylline, flunisolide, isoetharine, metaproterenol, oxtriphylline, terbutaline, theophylline, ephedrine pseudoephedrine, phenylephrine and norepinephrine. The composition is delivered by an atomizer means such as a liquid sprayer or inhaler to treat nasal congestion and asthmatic attacks.

Further provided by the invention is a cardiovascular and respiratory stimulating composition for administration to a patient in doses, the composition comprising a pharmacologically effective concentration of (+)naloxone in a carrier solution. If necessary, the composition may also contain a pharmacologically effective amount of at least one adrenergic agonist selected from the group consisting of epinephrine, isoproterenol, albuterol, aminophylline, beclomethasone, dyphylline, flunisolide, isoetharine, metaproterenol, oxtriphylline, terbutaline, theophylline, ephedrine pseudoephedrine, phenylephrine and norepinephrine.

The dose of the composition is metered to deliver, for example, between about 0.01 and 5 µg/mL of the adrenergic agonist and between about 0.1 and 6 µg/mL of (+)naloxone. The dose can be delivered via syringe into a blood vessel of the human, orally, or through an inhaler. The dose is delivered to the human during a stressful event where a boost of energy is required to enhance survival. For both injectable and breathable compositions, a carrier solution is used which is typically distilled water and isotonic NaCl adjusted to the desired pH. Additives such as stabilizers, moisturizers, flavor/smell enhancers, or other additiives may be used. The composition is typically sterile when used.

The method of administering (+)naloxone is also useful for concentrating or maintaining the concentration of another pharmaceutical agent at a local therapeutic target (e.g. skin, wound, oral cavity, local nerve, topical site) or restrict its spread to other sites to prevent toxic or unwanted consequences. Thus, the present invention is also a method of enhancing local vasoconstriction and serve as an adjuvant administered with other pharmaceuticals in order to contain those pharmaceuticals in a high therapeutically effective concentration at their site of administration. The method comprises delivering a pharmacologically effective dose of (+)naloxone in a carrier solution, the (+) naloxone thus creating a first composition in the saline solution. The effective dose of (+)naloxone is administered topically or by injection into the skin or a blood vessel via a syringe in combination with the pharmaceutical agent, or immediately before or after injection or application.

Additional objects, features and advantages will be apparent in the written description which follows.

BRIEF DESCRIPTION OF THE DRAWINGS

The novel features believed characteristic of the invention are set forth in the appended claims. The invention itself however, as well as a preferred mode of use, further objects and advantages thereof, will best be understood by reference to the following detailed description of an illustrative embodiment when read in conjunction with the accompanying drawings, wherein:

DETAILED DESCRIPTION OF THE INVENTION

Figure 1:
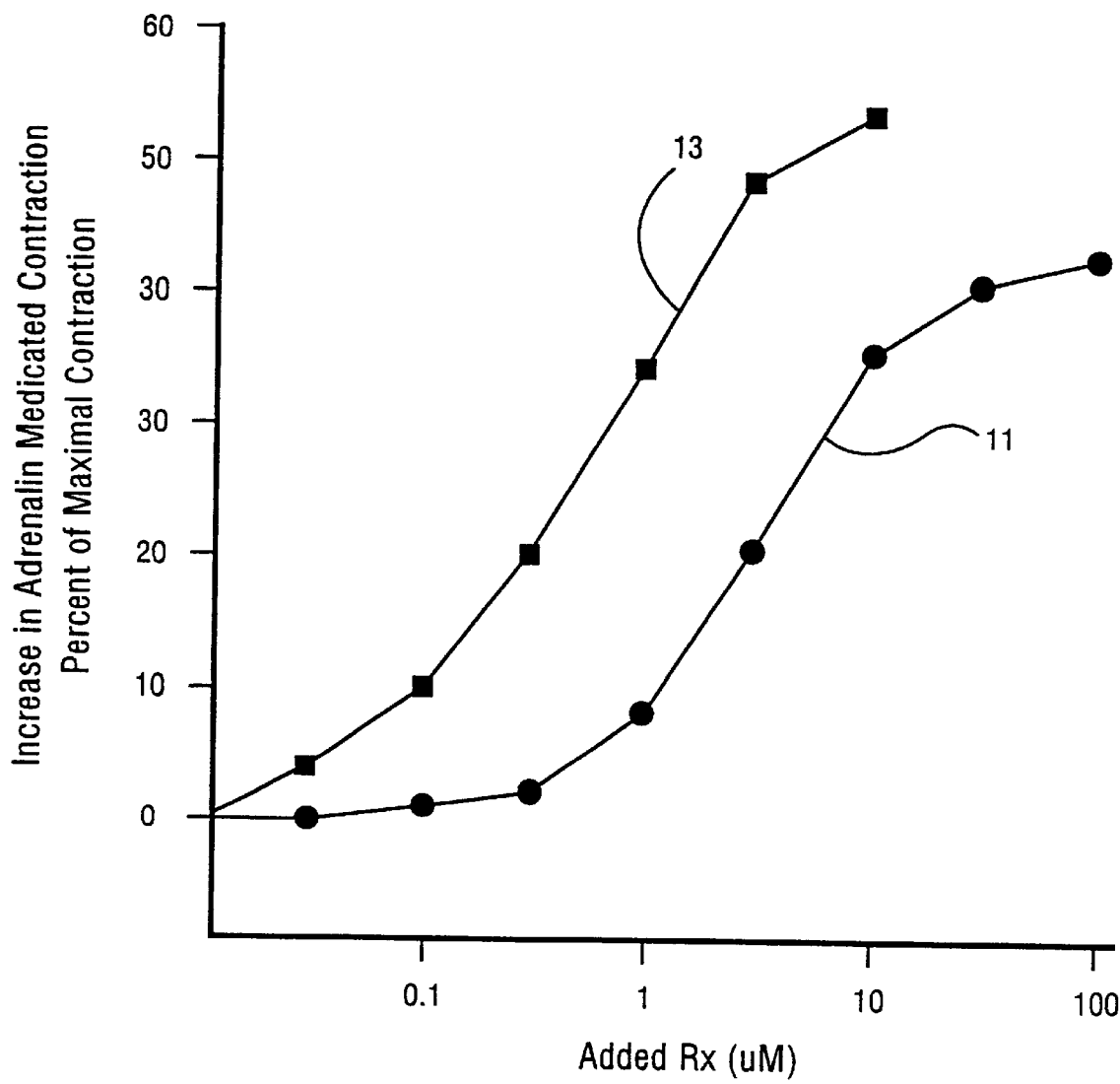
FIG. 1 is a graphical representation of data showing the effects of (+)naloxone and (+/−)naloxone [labeled (−)naloxone] on epinephrine-treated dog vessels.

The present invention is directed towards a method of alleviating breathing passageway compromise in humans and the pharmacological composition therein. The invention is based on part on the discovery that the positive enantiomer of naloxone, an opiate antagonist [(+)naloxone], provides a potentiating influence upon adrenergic agonists such as catecholamines and other bronchodilators of natural and synthetic origin. Hereinafter, the term "adrenergic agonist", "agonist", or "catecholamine" will be used to refer to both synthetic and naturally occurring compounds that are bronchodilators, sympathomimetics, or adrenergic agonists. The combination of (+)naloxone with adrenergic agonists acts synergistically to reduce the amount of agonist otherwise necessary for a given treatment in human patients, in particular in the treatment of breathing passageway compromise. Breathing passageways are referred to in general with reference to nasal passageways, sinuses, the larynx, lungs, bronchiole tubes, and other airways associated with humans.

The method of treating breathing passageway compromise is carried out by providing composition, and delivering that composition in a desirable manner to either the lungs or nasal passageway. The composition comprises a buffered saline solution of pH between about pH 2 and pH 7, the solution containing (+)naloxone and a pharmacologically effective concentration of at least one adrenergic agonist. The (+)naloxone and at least one agonist form a mixture in the saline solution, wherein the mixture may either be a complete suspension, a complete solution, or a mixture that is partially in solution and partially in suspension.

The composition of the invention comprises at least one adrenergic agonist such as a catecholamine or bronchodilator (hereinafter referred to in general as "adrenergic agonist" or "agonist"). More specifically, the at least one adrenergic agonist is selected from the group consisting of epinephrine, isoproterenol, albuterol, ephedrine, aminophylline, beclomethasone, dyphylline, flunisolide, isoetharine, metaproterenol, oxtriphylline, terbutaline, theophylline, pseudoephedrine, phenylephrine and norepinephrine. Further, mixtures of adrenergic agonists can be used. In the preferred embodiment of the invention, epinephrine is used in the composition. The composition is delivered to the human in doses from an appropriate atomizing means, the atomizing means being any such apparatus as a liquid sprayer, inhaler, or other device designed to create a mist or fog of a homogeneous or heterogeneous liquid and deliver that mist or fog to the appropriate breathing passageway or passageways of the human. Many compounds, especially naloxone, are readily absorbed through the nasal mucosa, and methods of delivering such compounds through the nasal passageway are disclosed in U.S. Pat. No. 4,464,378, herein incorporated by reference.

The atomizing means of the present invention should be calibrated in conjunction with the concentration of (+)naloxone and adrenergic agonist in the composition in order to provide the desired dose as determined by a trained practitioner. Typically, a dose is metered to deliver between about 0.01 and 5 μg/mL of the adrenergic agonist. Further, the dose is metered to deliver between about 0.1 and 6 μg/mL of (+)naloxone. In a preferred embodiment, between about 0.5 and 2 μg/mL of each component is metered per dose. Once breathed in by the human patient into the nose or into the lungs, the ingredients are then absorbed into the vocal tissues and into the blood stream, wherein its pharmacological influence takes place, typically an inotropic effect upon blood vessels associated with the breathing passageway and a relaxing effect on the muscles around the airways.

The present invention also provides a method and composition therein for stimulating cardiovascular and respiratory output in a human during high-stress situations. High-stress situations in encountered by emergency personnel, soldiers in military combat, and others often elicits the body's natural "fight or flight" response wherein epinephrine (adrenaline) is released into the bloodstream. This is beneficial as it improves blood and energy flow to muscle tissue. The present invention incorporates the discovery of (+)naloxone's potentiating influence on adrenergic agonists such as epinephrine to further stimulate human performance without the detrimental side effects of adding further amounts of adrenergic agonist.

The method involves delivering to the human in an emergency situation a pharmacologically effective dose of (+)naloxone in a buffered saline solution of pH between about pH 2 and pH 7, and preferably between about pH 6 and 7 in the case of injected composition. The (+) naloxone thus creates a first composition in the saline solution. While not typically necessary, the invention further provides in the first composition a pharmacologically effective amount of at least one adrenergic agonist selected from the group consisting of epinephrine, isoproterenol, albuterol, ephedrine and norepinephrine, creating a second composition. Typically, the dose of the adrenergic agonist in this instance is relatively small. Typically, a dose is metered to deliver between about 0.01 and 5 μg/mL of the adrenergic agonist, and a dose is metered to deliver between about 0.1 and 6 μg/mL of (+)naloxone. In a preferred embodiment of this aspect of the invention, a dose of the agonist is metered to deliver between about 0.01 and 1 μg/mL.

There may be one of several modes of delivery of the (+)naloxone, and if present, the agonist. The first or second compositions can be administered via injection directly into the blood stream of the human, or can be taken into the lungs of the human. To be taken into the lungs, an atomizer means such as an inhaler is used. The preferred pH range for injectable composition that allows the greatest stability for the (+)naloxone is between about pH 3 to 3.5 as disclosed in U.S. Pat. No. 5,866,156, herein incorporated by reference. For composition that is inhaled or delivered to the nasal passageway, the preferred pH is between about pH 5 and 7.

Epinephrine is one of the neural hormones responsible for the regulation of the heart, blood pressure, airway resistance, and energy metabolism. Epinephrine creates an inotropic effect, wherein it increases the heart rate, the force of contraction of the heart, narrows the blood vessels thus increasing blood pressure, reduces airway resistance to make it easier to breath, and raises blood glucose and blood fatty acids to supply the body energy during stress. Epinephrine also has uses as a drug which can be administered through the breathing passageways and/or directly into the blood stream. It's use as a drug include:

Combating low blood pressure during hemorrhagic or allergic shock;

Opening the airways during asthmatic attack;

Restricting the distribution of locally administered drugs such as local anesthetics;

Reducing nasal congestion; and

Performance aid in emergency situations.

While epinephrine and other catecholamines and adrenergic agonists may have potential uses as drugs, the harmful side effects of using these agonists may be contraindicated in many situations, especially for prolonged use. Some problems associated with the use of most adrenergic agonists include increasing heart rate when an opening of the airways is desired, a loss of efficacy (a desensitization or tachyphylaxis), and collateral ischemic damage due to depletion of tissue fuels.

It has been discovered that (+)naloxone potentiates the inotropic effects of adrenergic agonists, while avoiding the detrimental effects of the racemic mixture of naloxone in increasing pain sensation, especially when opiate drugs are also in use in the patient to be treated by the invention. Thus, when used as a combination therapy, less adrenergic agonist is necessary, hence smaller doses, when used in a synergistic combination with (+)naloxone. In fact, in emergency situations where the person is subject to stress, (+) naloxone alone may suffice and no additions or doses of adrenergic agonists may be necessary.

The combination therapy using (+)naloxone with epinephrine is further described with reference to FIGS. 1 and 2, wherein data demonstrate the synergistic effect of method of the invention and composition therein. The data in FIG. 1 are from experiments performed upon renal interlobar arteries of adult mongrel dogs. Specifically, referring to the data in FIG. 1, renal interlobar arteries were dissected free and 4 mm segments were cut and arranged on the base of opposing stainless steel triangles for later suspension. Vessel segments averaged 1 mm in diameter and 3–4 mg in weight. Vessels were used within 48 hrs. The vessels were pre-contracted with 10–25% of maximum with epinephrine ($2.5$–$5.0 \times 10^{-8}$ M) and then graded additions of naloxone were added sequentially to construct a cumulative dose response as in FIG. 1.

In general, it is expected that epinephrine, like most adrenergic agonists, will cause mammalian blood vessels to contact to one extent or another. This vessel response is a general response expected for most blood vessels in mammals, and would be expected for vessels within the nasal passageways and lungs of humans.

The data in FIG. 1 demonstrate the synergistic effects of the combination therapy of using (+)naloxone with an adrenergic agonist such as epinephrine. The curve 11 represents data wherein the racemic mixture of naloxone was added to epinephrine pretreated vessels, whereas the data in curve 13 represent the additions of (+)naloxone to the pretreated vessels. The (+)naloxone shows a 0.5–10 fold increase in epinephrine mediated vessel contraction when compared to the racemic mixture of naloxone added to epinephrine pre-treated vessels. Furthermore, for the same percent change, 5–10 fold less of naloxone was needed when (+)naloxone is used. The result is that 2–3 fold less epinephrine was needed to produce the same effect when (+)naloxone was used.

Figure 2:
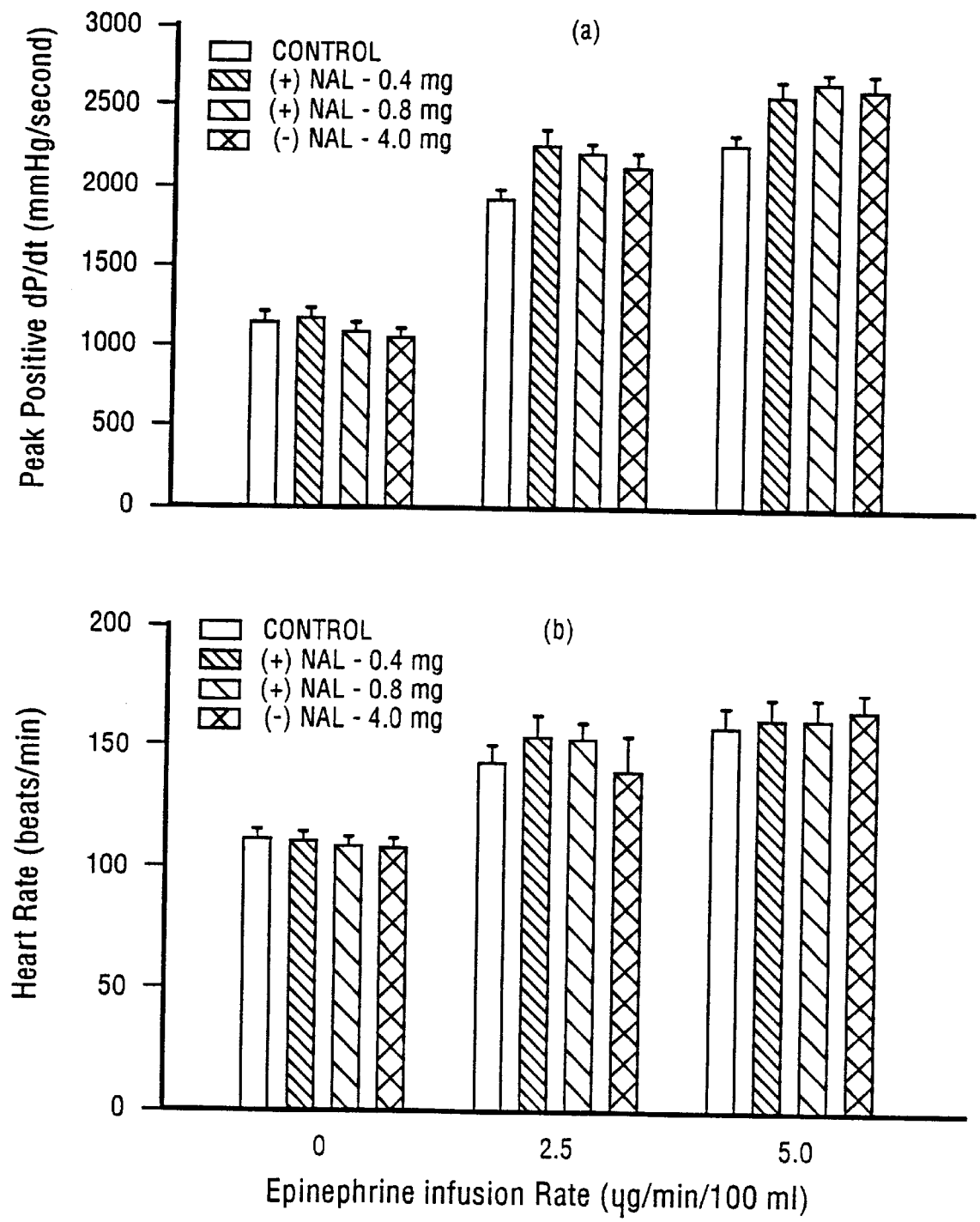
FIG. 2 is a graphical representation of data showing the effects of (+)naloxone and (+/−)naloxone [labeled (−)naloxone] on the heart rate and ventricular pressure in dog heart pre-treated with epinephrine.

The data in FIG. 2 give describe the effects of the (+/−) and (+) enantiomers of naloxone on cardiac function. In these data, the cardiac function of mongrel dogs was measured as a function of epinephrine and naloxone treatment. In these data, the left common coronary artery blood flow was measured, wherein epinephrine (5 $\mu$g/min/10 mL) was first infused briefly into the artery to determine the resulting increase in blood flow followed by several adrenergic challenges consisting of two intracoronary infusions of epinephrine at 2.5 and 5 $\mu$g/min/100 mL, respectively, for 3 min each, or infusions of 0.75 $\mu$g/mL and 1.5 $\mu$g/mL, respectively. After a 45 min recovery time following the each challenge of epinephrine, the artery was then infused with naloxone at 0.4 mg, 0.8 mg, and 4 mg doses and the epinephrine challenges were repeated.

These data are represented in FIG. 2, wherein it is shown that additions of (+)naloxone and epinephrine, when compared to the control experiment where no naloxone was added, increased both the heart rate and peak positive rate of change in left ventricular pressure (dP/dt). This effect is greater with the (+)naloxone enantiomer than with the racemic naloxone mixture. The data also show that this effect is also achieved at a much lower dose of (+)naloxone than required for the racemic mixture and the lower dose of the (+)naloxone gives a maximal response, with little added effect at higher (0.8 mg) doses.

The data in FIG. 2 show that (+)naloxone has a synergistic effect with epinephrine. For instance, heart rate response to epinephrine is maximal at an infusion rate of 2.5 $\mu$g/min/10 mL in the presence of (+)naloxone—doubling the epinephrine infusion rate was required to produce the same response without (+)naloxone (infusion rate of 5 $\mu$g/min/10 mL, control sample). Further, the peak dP/dt was greater with only infusion of epinephrine when (+)naloxone is present. Thus, (+)naloxone greatly potentiates the effect of adrenergic agonists in dog heart.

The following examples of the present invention are described in order to show possible embodiments of the present invention and are by no means meant to be limiting of the invention itself.

EXAMPLE 1

Figure 3:
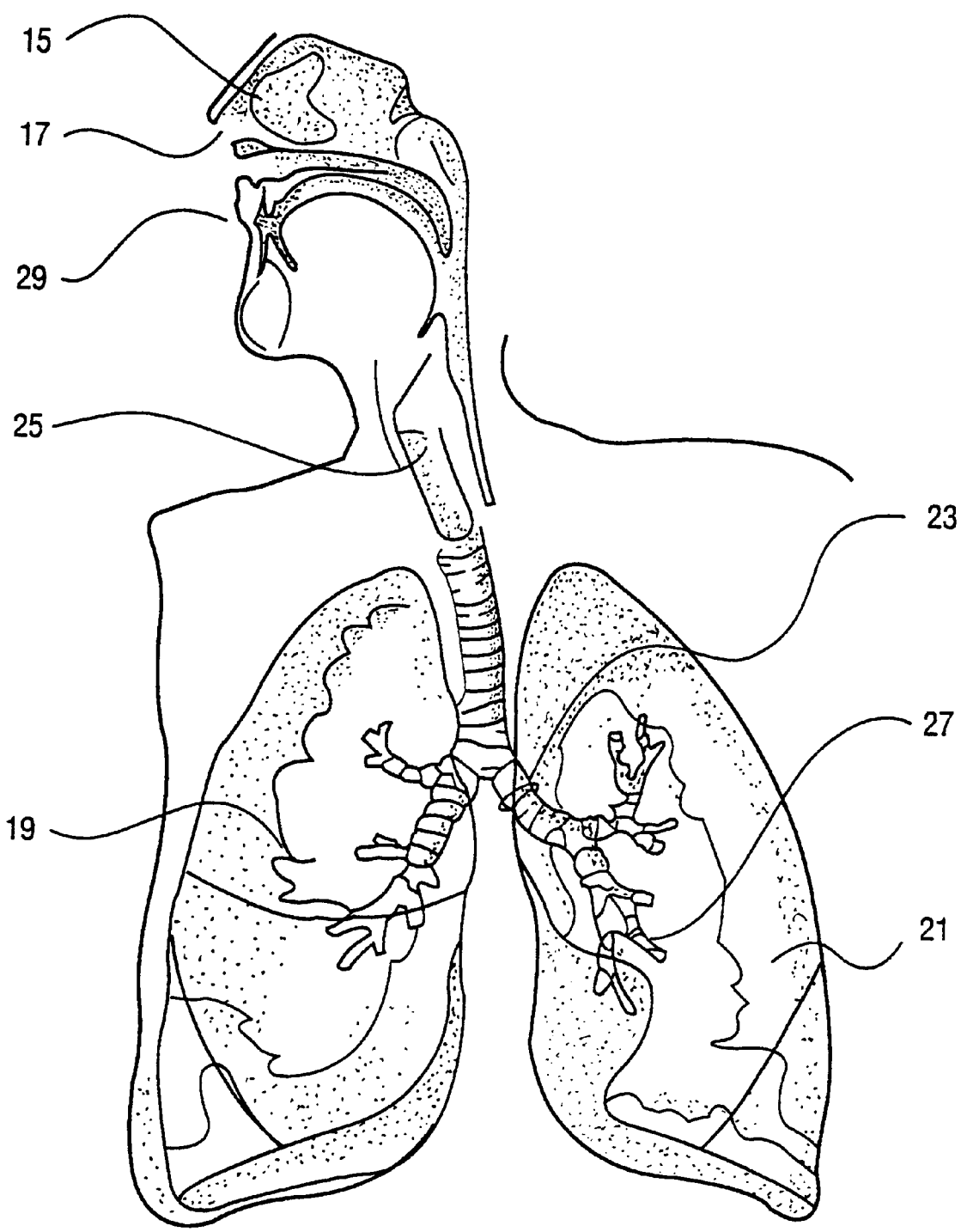
FIG. 3 is a drawing of the internal breathing passageways within a human.

Nasal Decongestant. The use of the present invention as a nasal decongestant is described with reference to FIG. 3, wherein the breathing passageways of a human are described. The dose or doses are delivered through the nostril(s) 17 into the nasal cavity 15. The mode of deliver is the use of an atomizing means such as a liquid sprayer. These liquid sprayers typically comprise a liquid reservoir and a dispensing means. In one type of dispenser, the dispensing means is simply a nozzle that creates a spray of liquid when liquid from the reservoir is forced through.

The reservoir of the liquid sprayer contains the composition of the invention. Typically, in a saline solution (0.02 M NaCl in distilled water), is mixed the (+)naloxone. The pH of the solution is typically between 5 and 7, and preferably at between about pH 6 to 7 in order to dissolve the (+)naloxone. Further, a stabilizer such as EDTA can be added, as well as gel-forming agents and buffers such as Tris-HCl or phosphate buffer. The resulting mixture may be a complete solution or a partial suspension, wherein the (+)naloxone may only be partially dissolved. The amount of (+)naloxone in the sprayer may vary depending upon the desired pharmacological effect. Typically, the sprayer will dispense enough of the mixture to deliver between about 0.1 and 6 $\mu$g/mL of (+)naloxone.

Further, the mixture also contains an adrenergic agonist, and in a preferred embodiment contains epinephrine. The epinephrine is added in such an amount to the liquid sprayer so that one dose will deliver between about 0.01 and 5 $\mu$g/mL of epinephrine. In a preferred embodiment, the dosage amount of both the (+)naloxone and epinephrine is between about 0.5 and 2 $\mu$g/mL. The dose may be varied depending upon the desired pharmacological effect by either adjusting the amount of component added to the liquid sprayer, and/or adjusting the metered dosage amount delivered from the liquid sprayer.

It is to be understood that a carrier other than saline could be used that, for example, contain organic liquids or a combination of water and organic liquids that is not buffered. Such a carrier solution would be used to form the mixture with the (+)naloxone and epinephrine or other agonist. For compositions that are to be inhaled or delivered into the nasal passageway, preferably about 0.4 mg (+)naloxone per mL of distilled water mixture is prepared, and enough HCl is added to bring the pH to between about pH 5 to 7. Enough NaCl is added to make the solution isotonic. Stabilizer may also be added as above. To sterilize the solution, the solution is passed through a 0.2 micron Millipore filter.

Once the desired dosage is identified by a practitioner, the subject patient would then deliver the metered dose into their nostril(s) 17, the mixture making contact with the inside surface of the nasal cavity 15, wherein it is absorbed by the capillary vessels surrounding the tissues. The therapy of the invention will improve vascular smooth muscle contractions, wherein less adrenergic agonist is added than would be otherwise required and allowing blood vessels on the nasal passages to contract and the airways to open without undue blood vessel contraction that can cause ischemic-like damage of surrounding tissues.

EXAMPLE 2

Asthma Attack. The use of the present invention as a treatment for asthma attack is described with reference to FIG. 3, wherein the breathing passageways of a human are described. An atomizing means such as an inhaler contains the composition of the invention, the fog or mist of the composition being pulled into the lungs 19 and 21 by negative pressure created by the patient. The inhaler is held at the mouth 29, wherein the negative pressure created by the user helps to pull or draw the mist or fog of composition into the larynx and ultimately into the lungs 19 and 21, and more specifically into the bronchus tubes 23, and segmental bronchus 27, and ultimately to the alveoli, wherein surrounding capillary beds can absorb the composition.

The inhaler may be any type of portable or non-portable atomizing means. For example, the composition may be pressurized in a metal canister by a gas such as $CO_2$, wherein a nozzle will release the mixture within the canister into the desired location, in this case the mouth and lungs. The composition may also be in a canister fitted with a pump-type delivery nozzle, wherein the user applies pressure on a pump to deliver the required dose. Also, the atomizing means can be such an apparatus as a battery or AC powered inhaler, wherein a fog or mist is created from the composition using an external pressurized air source purging through an atomizer containing the composition added by the user, the user then holding his mouth 29 and nostril 17 near an exhaust port on the atomizer wherein the fog or mist exits, the user then breathing in the mist or fog of composition.

The composition can be in a general carrier of either water, or a water and organic liquid solution with or without a buffer. Preferably, the composition is in a saline solution buffered to between about pH 3 and 7, and preferably between about pH 3 to 7 when injectable or between about pH 5 and 7 when inhaled or taken into the nasal passageway. The pH can be maintained with a buffer such as described in Example 1, and can contain gel-forming substances, EDTA, and other stabilizing agents. Various other additives can be used such as Benzyl alcohol, Eucalyptol, propylene glycol, and other additives appropriate to enhance the appeal or comfort of nasal inhalants such as disclosed in U.S. Pat. No. 5,854,269, herein incorporated by reference.

For compositions that are to be inhaled or delivered into the nasal passageway, preferably about 0.4 mg (+)naloxone per mL of distilled water mixture is prepared, and enough HCl is added to bring the pH to between about pH 5 to 7. Enough NaCl is added to make the solution isotonic. Stabilizer may also be added as above. To sterilize the solution, the solution is passed through a 0.2 micron Millipore filter.

The (+)naloxone and adrenergic agonist are added to the carrier. The resulting mixture may be a complete solution or a partial suspension, wherein the (+)naloxone may only be partially dissolved. The amount of (+)naloxone in the sprayer may vary depending upon the desired pharmacological effect. Typically, the sprayer will dispense enough of the mixture to deliver between about 0.1 and 6 μg/mL of (+)naloxone.

Further, the mixture also contains an adrenergic agonist, and in a preferred embodiment contains epinephrine, albuterol or other β-adrenergic agonist. The epinephrine is added in such an amount to the liquid sprayer so that one dose will deliver between about 0.01 μand 5 μg/mL of epinephrine. In a preferred embodiment, the dosage amount of both the (+)naloxone and epinephrine is between about 0.5 and 2 μg/mL. The dose may be varied depending upon the desired pharmacological effect by either adjusting the amount of component added to the inhaler, and/or adjusting the metered dosage amount delivered from the inhaler.

EXAMPLE 3

Performance Enhancer. A first composition containing (+)naloxone and a carrier, can be used as a performance enhancer, wherein the composition would be delivered through some means to the user who is in need of a boost of energy. The mode of delivery can be a direct injection via a syringe into a blood vessel, can be inhaled as in the asthma treatment, or may be some type of dermal patch device that delivers the composition transdermally.

In one embodiment of the invention, the performance enhancer first composition may be a saline solution at pH between about pH 5 and 7 for an inhaled mode of delivery, and containing enough (+)naloxone to deliver to the user between about 0.1 and 6 μg/mL. The amount delivered can be varied by altering the amount of the (+)naloxone on the dermal patch, or altering the injection via syringe, the injection dependent upon the initial concentration of the first composition to be injected. The pharmacologically effective dose will depend upon the situation, the body size of the user, the sex of the user, and other health factors that the practitioner must take into account in delivering the composition.

The carrier solution for injectable composition is preferably about 0.4 mg (+)naloxone per mL of distilled water, about 8.2–8.8 mg of NaCl, and enough HCl to bring the pH of the solution to about 3 to 7. EDTA or sodium edetate may also be added as a stabilizer, wherein the preferred amount of EDTA is between about 0.001% and 0.0001% by weight of the composition. This solution can be sterilized by either autoclaving or passing the mixture through a 0.2 micron Millipore filter. For composition that is to be inhaled or delivered into the nasal passageway, preferably about 0.4 mg (+)naloxone per mL of distilled water mixture is prepared, and enough HCl is added to bring the pH to between about pH 5 to 7. Enough NaCl is added to make the solution isotonic. Stabilizer may also be added as above. To sterilize the solution, the solution is passed through a 0.2 micron Millipore filter.

An adrenergic agonist may also be added to the first composition to create a second composition which may be desirable in certain situations and with certain users. In typical use, the user will be in an emergency situation and hence may not need any, or very little, agonist since the body is already releasing larger than normal quantities of the agonist. However, some situations may require the use of added agonist, preferably epinephrine or isoproterenol. The typical dosage is between about 0.01 and 1 μg/mL.

Once injected or otherwise delivered into the user, the first or second composition will act synergistically with the adrenergic agonist released within the user's body to increase heart rate and air flow though the breathing passageways. Further, glucose and fatty acids will be released to enhance the performance of the user. The addition of the (+)naloxone decreases the need for excessive amount of agonist, thus reducing the negative side effects of using adrenergic agonists.

EXAMPLE 4

Vaso-sequestering agent. The (+)naloxone may also be used to sequester and isolate other pharmaceuticals that are administered to a patient either topically or via injection. Thus, the invention is also a method of enhancing local vasoconstriction and serve as an adjuvant administered with other pharmaceuticals in order to contain those pharmaceuticals in a high therapeutically effective concentration at their site of administration. The method comprises delivering a pharmacologically effective dose of (+)naloxone in a carrier solution, the (+)naloxone thus creating a first composition in the saline solution. This first solution can be made as described above in the prior examples alone or in combination with adrenergic agonists, and administered with the other desirable pharmaceutical agent either topically or via syringe.

There are several advantages to the present invention. The invention increases the potency of epinephrine and other adrenergic agonists with respect to heart rate, contractile force, and blood pressure in the whole animal. This will allow physicians and practitioners to improve cardiac and circulatory performance with fewer side effects.

The present invention also improves the recovery of mammals from circulatory shock resulting from hemorrhage or bacterial toxins.

Another advantage to the present invention is that it reduces nasal congestion and airway resistance following exposure to histamine and potentiates the action of agonists or antihistamine in this regard. This could result in a more economical and more effective nasal decongestant and adjuvant therapy for asthma.

Yet another advantage to the present invention is that the (+)naloxone combined with epinephrine and other agonists better restricts the systemic distribution of locally administered drugs that epinephrine alone cannot. This would improve the efficacy of drugs as local anesthetics which one wants to restrict to a local target site and not allow access to the systemic circulation.

Yet another advantage to the present invention is that the use of (+)naloxone avoids the possibility of exacerbating pain responses in a human where endogenous opiates are at work, or when naloxone would be contraindicated due to the concurrent use of an opiate such as morphine when an adrenergic agonist is being administered.

Yet another advantage to the present invention is that the synergistic effect of (+)naloxone with adrenergic agonists reduces the amount of agonist that would otherwise be needed by at least 2–3 fold, hence avoiding a tachyphylaxis response in the user. Also, ischemic or ischemic-like tissue damage may be avoided since less agonist is needed for a given treatment, hence, less constriction of the blood vessels will ensue.

Yet another advantage to the present invention is the ability of the (+)naloxone therapy to enhance local vasoconstriction and serve as an adjuvant administered along with other pharmaceuticals to localize and hence improve their effect, while limiting potential side effects from the pharmaceutical spreading to other parts of the body.

While the invention has been shown in only one of its forms, it is not thus limited but is susceptible to various changes and modifications without departing from the spirit thereof.

What is claimed is:

1. A composition formulated for dose-wise delivery to a breathing passageway of a human, the composition comprising:

a carrier solution, the solution containing (+)naloxone; and the solution also including a pharmacologically effective amount of at least one adrenergic agonist, the (+)naloxone and agonist forming a mixture in the carrier solution.

2. The composition of claim 1, wherein a dose is metered to deliver between about 0.01 and 5 µg/mL of the adrenergic agonist.

3. The composition of claim 1, wherein a dose is metered to deliver between about 0.1 and 6 µg/mL of (+)naloxone.

4. The composition of claim 1, wherein the at least one adrenergic agonist is a catecholamine.

5. The composition of claim 1, wherein the at least one adrenergic agonist is selected from the group consisting of epinephrine, isoproterenol, albuterol, aminophylline, beclomethasone, dyphylline, flunisolide, isoetharine, metaproterenol, oxtriphylline, terbutaline, theophylline, pseudoephedrine, phenylephrine ephedrine and norepinephrine.

6. The composition of claim 1, comprising two adrenergic agonists.

7. The composition of claim 1, further comprising a preservative.

8. The composition of claim 1, wherein the carrier is a buffered saline solution of pH between about pH 5 and pH 7.

9. The composition of claim 1, wherein the mixture is placed within a liquid sprayer for administration to the nasal passageway of a human for treatment of nasal decongestion.

10. The composition of claim 1, wherein the mixture is placed within an inhaler for administration to the lungs of a human for treatment of asthmatic attacks.

11. A cardiovascular and respiratory stimulating composition for administration to a patient in doses, the composition comprising:

a pharmacologically effective concentration of (+)naloxone in a carrier solution; and further comprising a pharmacologically effective amount of at least one adrenergic agonist selected from the group consisting of epinephrine, isoproterenol, albuterol, aminophylline, beclomethasone, dyphylline, flunisolide, isoetharine, metaproterenol, oxtriphylline, terbutaline, theophylline, pseudoephedrine, phenylephrine, ephedrine and norepinephrine.

12. The composition of claim 11, wherein a dose is metered to deliver between about 0.01 and 5 µg/mL of the adrenergic agonist.

13. A cardiovascular and respiratory stimulating composition for administration to a patient in doses, the composition comprising:

a pharmacologically effective concentration of (+)naloxone in a carrier solution; and wherein a dose is metered to deliver between about 0.1 and 6 µg/mL of (+)naloxone.

14. A method of alleviating breathing passageway compromise in humans, the method comprising:

providing a carrier solution, the solution containing (+)naloxone and a pharmacologically effective concentration of at least one adrenergic agonist, the (+)naloxone and at least one agonist forming a mixture in the saline solution;

wherein the mixture is contained in an atomizer means to direct an atomized fog of the mixture directly into at least one breathing passageway of the human;

directing a atomized fog dose of the mixture into the at least one breathing passageway of the human.

15. The method of claim 14, wherein the at least one adrenergic agonist is a catecholamine.

16. The method of claim 14, wherein the at least one adrenergic agonist is selected from the group consisting of epinephrine, isoproterenol, albuterol, aminophylline, beclomethasone, dyphylline, flunisolide, isoetharine, metaproterenol, oxtriphylline, terbutaline, theophylline, pseudoephedrine, phenylephrine ephedrine and norepinephrine.

17. The method of claim 14, comprising two adrenergic agonists.

18. The method of claim 14, wherein a dose is metered to deliver between about 0.01 and 5 μg/mL of the adrenergic agonist.

19. The method of claim 14, wherein a dose is metered to deliver between about 0.1 and 6 μg/mL of (+)naloxone.

20. The method of claim 14, wherein the atomizing means is a liquid sprayer for delivering the mixture to the nasal passageway of the human.

21. The method of claim 14, wherein the atomizing means is an inhaler for delivering the mixture to the lungs of the human.

22. The method of claim 14, wherein the carrier is a buffered saline solution of pH between about pH 5 and pH 7.

23. A method of stimulating cardiovascular and respiratory output in a human during high-stress situations, the method comprising:

delivering a pharmacologically effective dose of (+)naloxone in a carrier solution, the (+) naloxone thus creating a first composition in the saline solution.

24. The method of claim 23, wherein further provided in the first composition is a pharmacologically effective amount of at least one adrenergic agonist selected from the group consisting of epinephrine, isoproterenol, albuterol, aminophylline, beclomethasone, dyphylline, flunisolide, isoetharine, metaproterenol, oxtriphylline, terbutaline, theophylline, pseudoephedrine, phenylephrine, ephedrine and norepinephrine.

25. The method of claim 23, wherein the first composition is administered via injection directly into the blood stream of the human.

26. The method of claim 23, wherein the first composition is taken into the lungs of the human.

27. The method of claim 24, wherein a dose is metered to deliver between about 0.01 and 5 µg/mL of the adrenergic agonist.

28. The method of claim 23, wherein a dose is metered to deliver between about 0.1 and 6 µg/mL of (+)naloxone.

29. The method of claim 23, wherein the carrier is a buffered saline solution of pH between about pH 3 and pH 7.

30. A method of enhancing local vasoconstriction and serve as an adjuvant administered with adrenergic agonists and other pharmaceuticals in order to contain those pharmaceuticals in a high therapeutically effective concentration at their site of administration, the method comprising:

delivering a pharmacologically effective dose of (+)naloxone in a carrier solution, the (+) naloxone thus creating a first composition in the saline solution.

31. The method of claim 30, wherein the effective dose of (+)naloxone is administered topically.

32. The method of claim 31, wherein the effective dose of (+)naloxone is administered by injection into a blood vessel.

* * * * *